US005422688A

United States Patent [19]

Asea

[11] Patent Number: 5,422,688

[45] Date of Patent: Jun. 6, 1995

[54] EYE EXERCISING PROCESS AND APPARATUS

[76] Inventor: Michael S. Asea, 2 Stayman Pl., Glenwood, N.J. 07418

[21] Appl. No.: 535

[22] Filed: Jan. 4, 1993

Related U.S. Application Data

[63] Continuation of Ser. No. 707,680, May 30, 1991, abandoned, which is a continuation-in-part of Ser. No. 490,843, Mar. 9, 1990, abandoned.

[51] Int. Cl.[6] .................... A61B 3/00

[52] U.S. Cl. .................... 351/203; 351/247

[58] Field of Search .................... 351/203, 247; 128/76.5

[56] References Cited

U.S. PATENT DOCUMENTS

| | | | |
|---|---|---|---|
| 3,875,934 | 4/1975 | Sadanaga | 351/203 |
| 4,408,846 | 10/1983 | Balliet | 351/203 |
| 4,464,027 | 8/1984 | Cooper | 351/203 |
| 4,506,963 | 3/1985 | Cooper | 351/203 |
| 4,838,677 | 6/1989 | Bronskill et al. | 351/203 |
| 5,040,888 | 8/1991 | Bonham | 351/203 |

*Primary Examiner*—William L. Sikes
*Assistant Examiner*—Hung Xuan Dang
*Attorney, Agent, or Firm*—George A. Skoler

[57] ABSTRACT

A eye exercising process and apparatus for an individual focusing on a viewable object, such as a computer monitor or television screen, and causing the object through means to slowly reciprocate or oscillate, generally at a predetermined rate, whereby the viewer's eye muscles are exercised without visual distraction.

8 Claims, 2 Drawing Sheets

EYE EXERCISING PROCESS AND APPARATUS

RELATED APPLICATIONS

This is a continuation of copending application Ser. No. 07/707,680 filed on May 30, 1991, now abandoned, which application is a continuation-in-part of U.S. patent application Ser. No. 490,843, filed Mar. 9, 1990, now abandoned.

BRIEF DESCRIPTION OF THE INVENTION

A eye exercising process and apparatus for an individual focusing on a viewable object, such as a computer monitor or television screen. The process and apparatus involves slowly reciprocating the object, generally at a predetermined rate, whereby the viewer's eye muscles are exercised without visual distraction.

BACKGROUND TO THE INVENTION

There is growing recognition that computer use and television viewing in which the viewer focuses on a fixed screen, impairs the viewer's vision. It is thought that luring ones eyes on a set object for a long period of time weakens the eye muscles and thus impairs vision.

A holistic view to correcting visual impairment is to exercise the eye. The proposed techniques involve, generally, a pattern of eye muscle relaxation followed by eye stress. Recently, a computer software has been developed to provided eye exercises. Such a system requires the user to commit to concentrating on use of the program for the benefits it is to provide, with consequent nonuse of other computer programs from which ones livelihood is derived.

Some experts assert that video display terminals induce pseudo-myopia (the inability to change focus from near to far, causing blurred distance vision). This problem and others, have generated a number of cure proposals. A variety of exercises have been developed, leading to the creation of a small health industry dedicated to eye correction through exercise. Though careful scientific studies are needed to support claims of the benefits from eye exercise, there is enough anecdotal evidence to give credence to assertions that eye exercise improves vision.

The techniques presently employed for exercising the eye employ conscious interactive and nonpassive systems. This means that the patient is consciously aware of the exercise activity and his/her interaction with it. In addition, the patient actively and consciously engages in the eye exercise. Such techniques require the patient to dedicate specific periods of time to the activity and this, of course, detracts from work and recreational time.

There is a need for a process that allows one to do eye exercise without interrupting work and recreational activities, in fact, make the exercise an integral part of these activities. It would be desirable that this process occur without creating the perception in the patient's mind that he/she was engaged in an exercise program. However, the ultimate process would achieve this without the patient consciously appreciating that he/she is undergoing an eye exercise program.

These advantages and more are accomplished by this invention.

THE INVENTION

The invention relates to a eye exercising process and apparatus. The process involves an individual focusing on a viewable object, such as a computer monitor or television screen, and causing the object through means to slowly oscillate or reciprocate, generally at a predetermined rate, whereby the viewer's eye muscles are exercised without visual distraction. The apparatus provides accommodating the process.

To make the exercise effective, the object's motion is limited so as to make viewing physically comfortable yet fast enough that there is effective eye exercise. It has been determined that a back and forth or side to side oscillating or reciprocating rate of about 5 inches per minute, such as a rate of about 2.5 to about 7.5 inches per minute, is a satisfactory exercise rate. Such a rate does not create a work or leisure distraction yet adequately exercises the eye muscles.

The essence of the invention is the slow movement of a viewable object that a person views for extended periods of time in a pattern that exercises the eye muscles. In its most favorable embodiment, the process uses TV screens or computer monitor screens as the viewable object, especially computer monitors.

In the preferred embodiment, the viewable object is about 18 to about 30 inches from the viewer and the apparatus of the invention is situated such that the mean of the reciprocating or oscillating distance is fixed to that average distance. The reciprocating or oscillating distance is chosen on the basis of the relationship of the viewer's comfort to the degree of discomfort occasioned by the exercise. The distance should be long enough that tangible eye muscle exercise is achieved but not so long as to cause unacceptable viewer discomfort. Since each person has a unique discomfiture threshold, a certain amount of experimentation is required on a case by case basis to determine the proper distance.

DETAILED DESCRIPTION OF THE INVENTION

A considerable amount of most people's leisure and/or work time is spent in front of a television or computer monitor. This is especially the case with computer users. These screens offer the user little eye activity. Even an action movie on television offers less than a desirable amount of eye muscle exercise for the viewer. Computer screens, essentially devoid of visual movement, will actually induce eye muscle atrophy. The situation is so severe that local governments are legislating the amount of time people spend on computers in work related activities. There is a need to couple with these activities an eye exercise capability that does not detract from their functional capabilities. This invention achieves that need by introducing an eye exercise that does not interfere with the work activity and sends "subliminal" messages to the eye that exercise the eye muscles.

Figure 1:
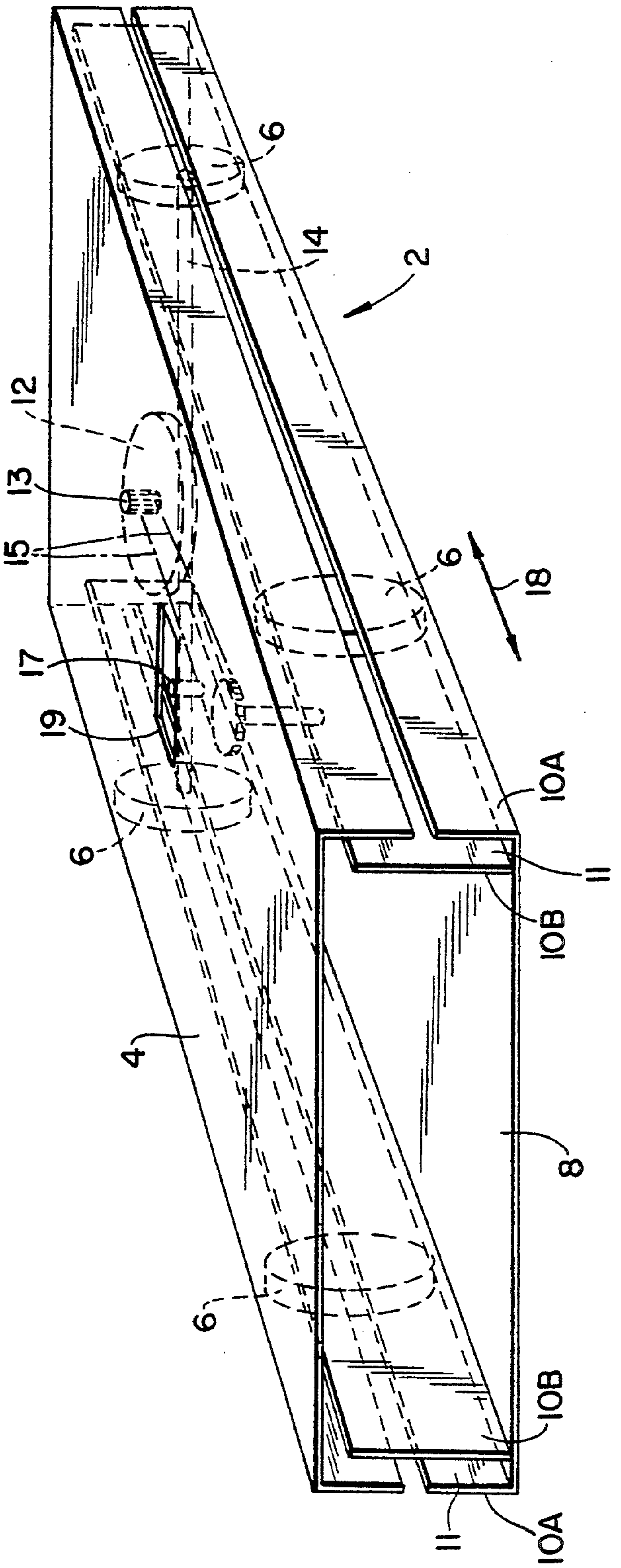
FIG. 1 is a perspective view of an apparatus for controlled reciprocation of a viewable object.

FIG. 1 shows an apparatus, 2, that allows for slow oscillation or reciprocation of a viewing object such as a television set or monitor, or computer monitor. Apparatus 2 comprises a stationary base 8 over which sits movable support surface 4 secured to bearings 6 via conventional means such as axles, spindles, posts and the like. Base 8 contains pairs of outside walls, 10A and 10B, forming trough's 11 in which bearings 6 ride. In the case of the rear bearings 6, they may be fastened to axle 14, so that their rotation, direction and rate, are controlled by the rotation direction and rate of rotation of axle 14, if axle 14 is chosen as the means for creating and controlling the oscillating motion indicated by directional arrow 18. If axle 14 is used for this purpose, then it would be connected to a variable or fixed speed electric motor 12 (electric outlet or battery connection not shown) through a conventional gear arrangement, not shown. Motor 12 may be part of the axle 14 assembly when arm portions forming axle 14 protrude from two rotors each extending from a different end of motor 12. The arms would be fixed to rear bearings 6 so as to drive the bearings in synchronization with the reciprocation of axle 14.

In another embodiment, bearings are fixed by posts to surface 4. In this embodiment, variable or fixed speed motor 12 is connected to sprocket 13, which it drives in a single direction at a predetermined or variable rate. Motor 12 is not, in this embodiment, connected to axle 14. Sprocket 13 engages link chain 15 which contains cam pin 17 which rides in cam slot 19. The length of slot 19 is sufficient on each ½ revolution of chain 15, pin 17 reverses its direction. This causes surface 4 to reverse its direction.

Figure 2:
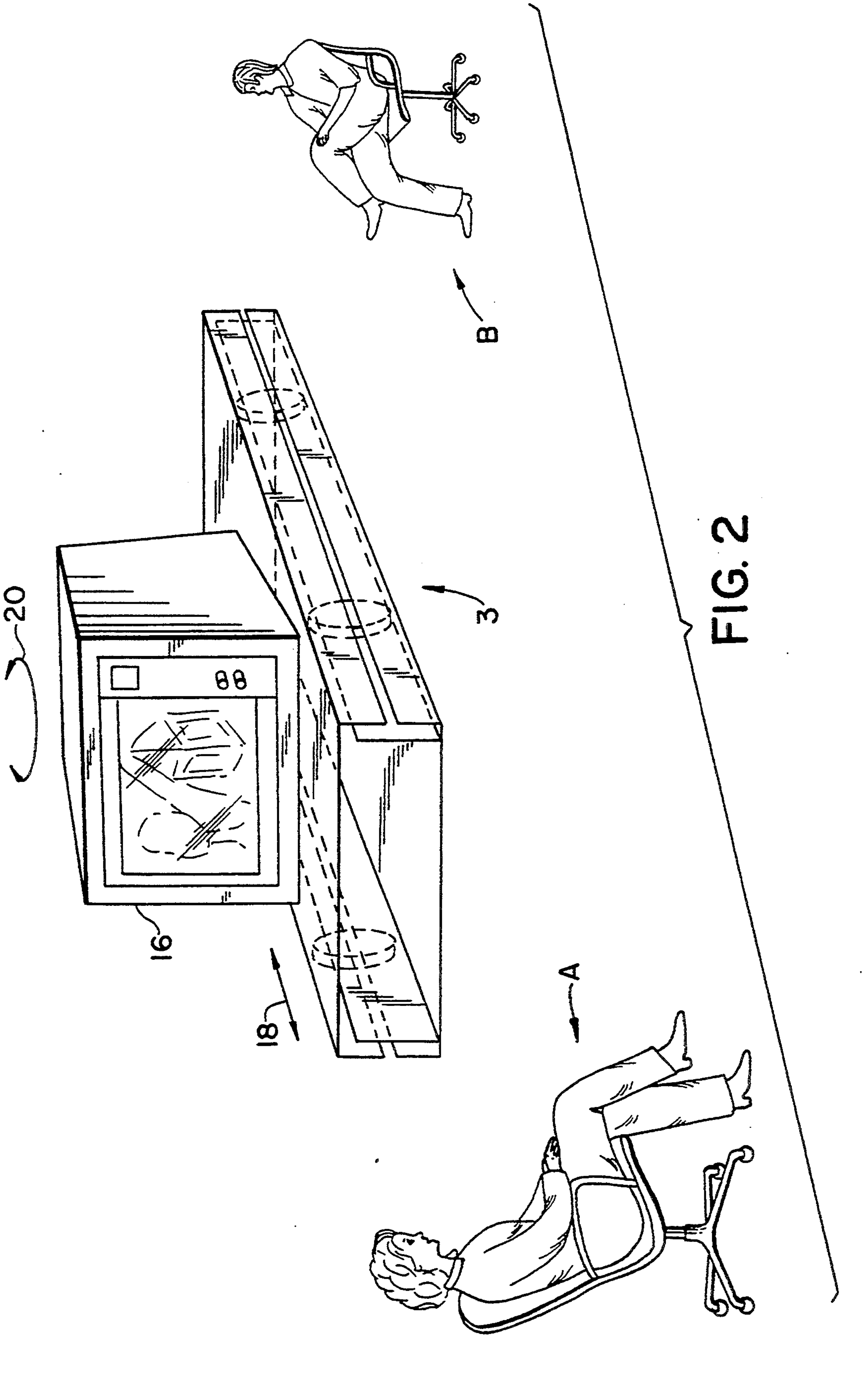
FIG. 2 is a perspective view of the apparatus of FIG. 1 on which is placed a computer monitor.

FIG. 2 shows the apparatus of FIG. 1 as an assembly 3 with computer monitor 16 and the relationship of that apparatus to viewers A and B. By the direction in which the viewing screen of monitor 16 faces the viewer, and as indicated by directional arrows 20, that may be in any direction at the option of the viewer, eye exercise is obtained by forward and backward movement, side to side movement or a combination of both. For example, viewer A will view the monitor moving back and forth whereas viewer B will view the monitor moving side to side. A viewer located between them will see the monitor moving both ways.

For example, apparatus 2 may be arranged so that a sidewall 10A faces the viewer and in that embodiment, the exercise is effected by a side to side motion. As shown in FIG. 2, the assembly achieves eye exercise by front to back motion.

I claim:

1. A process for exercising an individual's eye during use of a computer which comprises focusing the eye on a computer monitor during operation of the computer and the monitor while causing the computer monitor to move directly forward and back at a slow predetermined rate, without side-to-side movement whereby the viewer's eye muscles are exercised by the movement of the computer monitor without visual distraction.

2. The process of claim 1 wherein the computer monitor is not moved so fast as to make viewing physically uncomfortable nor so slow that there is essentially no effective eye exercise.

3. The process of claim 2 wherein the slow predetermined rate is about 5 inches per minute.

4. The process of claim 3 where the slow predetermined rate is about 2.5 to about 7.5 inches per minute.

5. The process of claim 1 wherein the slow predetermined rate is about 2.5 to about 7.5 inches per minute.

6. An eye exercise apparatus comprising a directly forward and back moving surface in combination with a computer monitor mounted thereon and means for slowly moving the surface with the mounted computer monitor at a predetermined moving rate without side-to-side movement.

7. The eye exercise apparatus of claim 6 wherein the apparatus comprises a stationary base over which sits a movable support surface for mounting the computer monitor, which surface is secured to bearings whereby the surface is capable of moving through the beatings on the base, and motorized means coupled to the apparatus for direct forward and back movement of the support surface at a predetermined rate.

8. The eye exercise apparatus of claim 7 wherein coupling of the motorized means to the support surface is through cam acting means that provide means to achieve direct forward and back movement of the surface.

* * * * *

UNITED STATES PATENT AND TRADEMARK OFFICE
CERTIFICATE OF CORRECTION

PATENT NO. : 5,422,688

DATED : June 6, 1995

INVENTOR(S) : Michael S. Asea

It is certified that error appears in the above-indentified patent and that said Letters Patent is hereby corrected as shown below:

In column 1, line 23, change "luring" to ---fixing---;

In column 4, line32, "beatings" to ---bearings---.

Signed and Sealed this

Twenty-ninth Day of August, 1995

Attest:

Bruce Lehman

BRUCE LEHMAN

Attesting Officer

*Commissioner of Patents and Trademarks*